United States Patent [19]

Commons et al.

[11] Patent Number: 5,401,769
[45] Date of Patent: Mar. 28, 1995

[54] DIBENZOFURANYL N-ALKYL CARBAMATES

[75] Inventors: Thomas J. Commons, Wayne, Pa.; Richard E. Mewshaw, Plainsboro, N.J.; Donald P. Strike, St. Davids, Pa.

[73] Assignee: American Home Products Corporation, Madison, N.J.

[21] Appl. No.: 190,402

[22] Filed: Feb. 2, 1994

[51] Int. Cl.⁶ .................. C07D 307/91; A61K 31/34
[52] U.S. Cl. ...................................... 514/468; 549/461
[58] Field of Search .................... 549/461; 514/468

[56] References Cited

U.S. PATENT DOCUMENTS

| | | | |
|---|---|---|---|
| 3,819,683 | 6/1974 | Krebs et al. | 546/222 |
| 3,846,445 | 11/1974 | Bondesson | 549/461 |
| 4,199,346 | 4/1980 | Saukaitis | 549/461 |
| 5,066,674 | 11/1991 | Quinn | 514/529 |

FOREIGN PATENT DOCUMENTS 454280 11/1973 Australia .
0116234 8/1984 European Pat. Off. .

*Primary Examiner*—Celia Chang
*Attorney, Agent, or Firm*—Richard K. Jackson

[57] ABSTRACT

A compound of formula A:

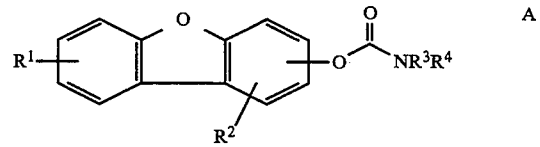

wherein $R^1$ and $R^2$ are, independently, hydrogen, fluorine, chlorine, bromine, iodine, trifluoromethyl, cyano, nitro, alkyl, alkoxy, —$CO_2H$, alkylcarbonyl, alkylcarbonyloxy, alkoxycarbonyl, alkoxycarbonyloxy, mono or dialkylaminocarbonyl, or mono or dialkylaminocarbonyloxy; $R^3$ is hydrogen or alkyl; $R^4$ is alkyl, cycloalkylalkyl or phenylalkyl or substituted phenylalkyl, and the substituent on the benzene ring is alkyl, alkoxy, halo, nitro, cyano, trifluoromethyl or phenyl, are anticholesterolemic agents.

10 Claims, No Drawings

DIBENZOFURANYL N-ALKYL CARBAMATES

BACKGROUND OF THE INVENTION

U.S. Pat. No. 3,819,683 discloses dibenzolfuryl N-methyl carbamate as an intermediate to be used in the preparation of an N-acylated final product of unknown utility.

DESCRIPTION OF THE INVENTION

In accordance with this invention there is provided a group of compounds of formula A:

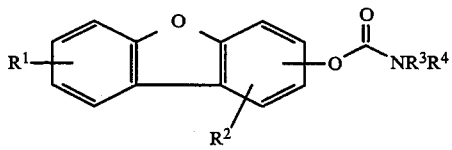

wherein $R^1$ and $R^2$ are, independently, hydrogen, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, $C_2$–$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$–$C_6$ alkyl;

$R^4$ is $C_2$–$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl.

The compounds of this invention inhibit the absorption of cholesterol from the intestinal tract. As indicated in Table I below, the compounds are inhibitors of cholesterol ester hydrolase (CEH). It has been shown that removal of this enzyme from pancreatic juice results in an 80% reduction in the uptake of cholesterol into the bloodstream in rats [Hosie et al, J. Biol. Chem., 262, 260 (1987)]. The association between high serum cholesterol levels and coronary heart disease is well documented. Consequently, compounds that prevent the uptake of cholesterol are useful for treating atherosclerosis, familial hypercholesterolemia, hyperlipemia, and like diseases.

Hence, this invention also provides a method for reducing cholesterol uptake from the intestinal tract which comprises administering, orally or parenterally, to an animal in need of reduced cholesterol absorption, a compound of formula B:

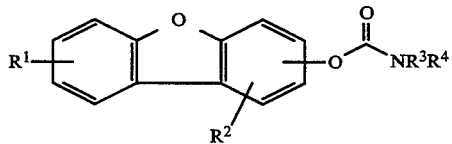

wherein $R^1$ and $R^2$ are, independently, hydrogen, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, $C_2$–$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$–$C_6$ alkyl;

$R^4$ is $C_1$–$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl.

In addition this invention provides pharmaceutical compositions comprising a compound of formula B:

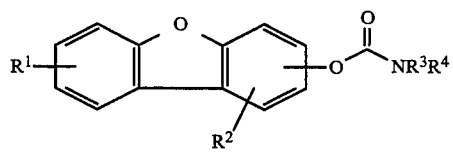

wherein $R^1$ and $R^2$ are, independently, hydrogen, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, $C_2$–$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$–$C_6$ alkyl;

$R^4$ is $C_1$–$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl;

and a pharmaceutically acceptable carder therefore.

The compounds of this invention are conveniently prepared by one of three methods. In the first method the hydroxydibenzofuran is reacted with the appropriate isocyanate in the presence of a base in a suitable solvent (Scheme I). In the second method the hydroxydibenzofuran is first converted in situ to its chloroformate using phosgene or a phosgene equivalent. Reaction of the chloroformate with the desired amine in the presence of a base in a suitable solvent gives the desired product. A suitable phosgene equivalent is trichloromethyl chloroformate (Scheme II). In the third method the hydroxydibenzofuran is converted to the nitrophenyl carbonate derivative shown in Scheme III. This compound is a convenient intermediate since it can be isolated as a stable crystalline solid. Reaction of the carbonate with the appropriate amine in the presence of a base in a suitable solvent then gives the desired product (Scheme III). Specific examples of the routes illustrated in Schemes I, II and III are given in the Experimental Section. These specific examples are for illustrative purposes only and are not to be construed as limiting to this disclosure in any way. Those skilled in the art will be aware of other methods of preparing compounds of this invention. The starting materials or intermediates are available commercially or can be prepared by standard literature procedures.

Scheme I

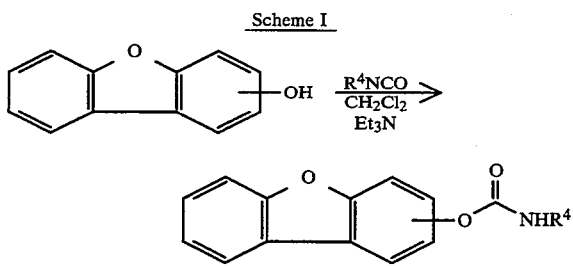

Scheme II

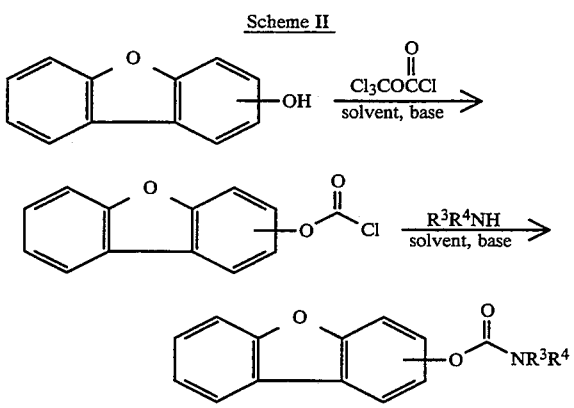

Scheme III

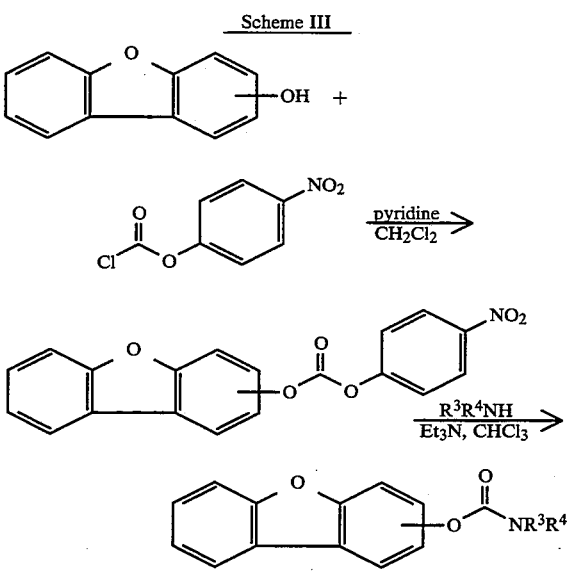

The in vitro and in vivo standard experimental test procedures used to establish the ability of the anticholesterolemic compounds of this invention to prevent cholesteryl ester formation and to inhibit cholesterol absorption, are given below and the biological results are presented in Table I.

In Vitro Test Procedure: The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.1.1.13) Sigma Company, St. Louis, Mo., U.S.A., No. C-1892, from bovine pancreas] and measuring the amount of ester formed, according to the procedure of Field, J. of Lipid Research, 25, 389 (1984). The concentration of test compound that inhibits one-half of the ester formation ($IC_{50}$) is given in Table I.

In Vivo Assay: The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20, 162 (1979). The serum radioactivity was measured at six hours after dosing. The results of this study are reported in the following Table I as percent decrease compared to control.

TABLE I

| Example | In Vitro Results $IC_{50}$ ($\mu$M) CEH | In Vivo Results Effect on Absorption of $^{14}$C-chol-6 hr- normal rat % Decrease (mg/kg) |
| --- | --- | --- |
| 1 | 25 | Not Determined |
| 2 | 3.0 | 33% (10) |
| 3 | 9.3 | 37% (10) |
| 4 | 68 | 44% (10) |
| 5 | 42 | Not Determined |
| 6 | 13.8 | 43% (10) |
| 7 | 7.2 ($IC_{25}$) | 13% (10) |
| 8 | 18.9 | 18% (10) |

EXPERIMENTAL SECTION

EXAMPLE 1

Butylcarbamic acid 2-dibenzofuranyl ester

A solution of 2-hydroxydibenzofuran (1.47 g, 7.98 mmol), butyl isocyanate (1.26 mL, 11.2 mmol) and triethylamine (0.89 mL, 6.39 mmol) in 50 mL of methylene chloride was stirred under $N_2$ at room temperature for 1 hour. The solvent was removed under reduced pressure to give a solid. Recrystallization from diethyl etherhexane gave 1.23 g (54%) of the title compound as a white crystalline solid, mp 124°–126° C.

Elemental analysis for $C_{17}H_{17}NO_3$ Calc'd: C, 72.10; H, 6.00; N, 4.94 Found: C, 71.88; H, 6.03; N, 5.13

EXAMPLE 2

(1.5-Dimethylhexyl) carbamic acid 2-dibenzofuranyl ester

A solution of 2-hydroxydibenzofuran (5.0 g, 27 mmol) and dimethylaniline (3.4 mL, 27 mmol) in 35 mL of benzene plus 1.5 mL of dioxane was added dropwise under nitrogen to a solution of trichloromethyl chloroformate (1.6 mL, 14 mmol) in 30 mL of benzene at ice bath temperature. After the addition the cooling bath was removed and the stirring continued for approximately 24 hours. The reaction was cooled to ice bath temperature and a solution of 1,5-dimethylhexylamine (4.6 mL, 27 mmol) and pyridine (4.4 mL, 54 mmol) in 30 mL of benzene was added dropwise over 15 minutes. After the addition the reaction was stirred at ice bath temperature for 2 hours. The cooling bath was removed and the stirring continued for approximately 22 hours. The reaction was extracted two times with 1N HCl. The organic solution was dried over anhydrous $MgSO_4$ and the solvent removed under reduced pressure to give 6.19 g of a yellow solid. Recrystallization from isopropanol gave 4.27 g (46%) of the title compound as a yellow crystalline solid, mp 114°–115° C.

Elemental analysis for $C_{21}H_{25}NO_3$ Calc'd: C, 74.31; H, 7.42; N, 4.13 Found: C, 74.22; H, 7.50; N, 3.98

EXAMPLE 3

Hexylcarbamic acid 2-dibenzofuranyl ester

A solution of 2-hydroxydibenzofuran (5.0 g, 27 mmol), hexyl isocyanate (4.1 g, 32 mmol) and triethylamine (3.0 mL, 22 mmol) in 75 mL of methylene chloride was stirred under nitrogen at room temperature overnight. The reaction was extracted with 1N HCl. The organic solution was dried (MgSO$_4$) and the solvent removed under reduced pressure to give 8.89 g of an off-white solid. Recrystallization of the solid from isopropanol gave 5.48 g (65%) of the title compound as an off-white crystalline solid, mp 109°–110° C.

Elemental analysis for $C_{19}H_{21}NO_3$ Calc'd: C, 73.29; H, 6.80; N, 4.50 Found: C, 73.12; H, 6.79; N, 4.48

EXAMPLE 4

(4-Phenylbutyl)carbamic acid 2-dibenzofuranyl ester

A solution of 2-hydroxydibenzofuran (5.0 g, 27 mmol) and dimethylaniline (3.4 mL, 27 mmol) in 35 mL of tetrahydrofuran plus 1.5 mL of dioxane was added dropwise under nitrogen to a solution of trichloromethyl chloroformate (1.6 mL, 14 mmol) in 30 mL of tetrahydrofuran at ice bath temperature. After the addition the cooling bath was removed and the stirring continued for approximately 24 hours. The reaction was cooled to ice bath temperature and a solution of 4-phenylbutylamine (4.3 mL, 27 mmol) and pyridine (4.4 mL, 54 mmol) in 30 mL of tetrahydrofuran was added dropwise over 15 minutes. After the addition the reaction was stirred at ice bath temperature for 2 hours. The cooling bath was removed and the stirring continued for approximately 22 hours. The reaction was diluted with ethyl acetate, extracted two times with 1N HCl, dried (MgSO$_4$) and the solvent removed under reduced pressure to give 6.47 g of a yellow solid. Purification of the solid by chromatography on silica gel (230–400 mesh) using hexane-methylene chloride as the eluent gave 1.28 g (13%) of the title compound as a white crystalline solid, mp 113°–114° C.

Elemental analysis for $C_{23}H_{21}NO_3$ Calc'd: C, 76.86; H, 5.89; N, 3.90 Found: C, 76.74; H, 6.03; N, 3.85

EXAMPLE 5

Methylcarbamic acid 2-dibenzofuranyl ester

A solution of 2-hydroxydibenzofuran (5.0 g, 27 mmol), methyl isocyanate (1.9 mL, 32 mmol) and triethylamine (3.0 mL, 22 mmol) in 75 mL of methylene chloride was stirred under nitrogen at room temperature overnight. During this time a solid formed. Additional methylene chloride was added and the solid dissolved. The reaction was then extracted with 1N HCl, dried (MgSO$_4$) and the solvent removed under reduced pressure to give 5.47 g of a yellow solid. Recrystallization from isopropyl ether gave 3.43 g (52%) of the title compound as a light brown crystalline solid, mp 155°–156° C.

Elemental analysis for $C_{14}H_{11}NO_3$ Cal'd: C, 69.70; H, 4.60; N, 5.81 Found: C, 69.90; H, 4.90; N, 5.13

EXAMPLE 6

(Cyclohexylmethyl)carbamic acid 2-dibenzofuranyl ester

In the same manner as described in Example 4, and replacing 4-phenylbutylamine with cyclohexylmethylamine, the title compound was produced as a white crystalline solid (0.832 g, 9%) after purification of the crude reaction product on silica gel using hexane-ethyl acetate as the eluent and recrystallization of the material isolated from ethyl acetate, mp 162°–163° C.

Elemental analysis for $C_{20}H_{21}NO_3$ Cal'd: C, 74.28; H, 6.54; N, 4.33 Found: C, 74.40; H, 6.86; N, 4.35

EXAMPLE 7

Dodecylcarbamic acid 2-dibenzofuranyl ester

A solution of 2-hydroxydibenzofuran (25 g, 0.136 mol) and pyridine (11 mL, 0.136 mol) in 300 mL of methylene chloride was added under nitrogen dropwise over five hours to a solution of 4-nitrophenyl chloroformate (27.4 g, 0.136 mol) in 300 mL of methylene chloride at ice bath temperature. After the addition the reaction was stirred at room temperature overnight. The solid formed was collected by filtration to give 33.08 g of a light tan solid. The filtrate was extracted one time with 1N HCl, one time with saturated Na$_2$CO$_3$ (emulsion formed), dried (MgSO$_4$) and the solvent removed under reduced pressure to give an additional 14.30 g of a light tan solid. This solid was triturated two times with methylene chloride to give 7.39 g of a light tan solid which was combined with the original 33.08 g of solid. Recrystallization of the combined material from ethyl acetate gave 20.23 g (43%) of carbonic acid (4-nitrophenyl) ester (2-dibenzofuranyl) ester as a light tan crystalline solid, mp 183°–185° C.

Elemental analysis for $C_{19}H_{11}NO_6$ Cal'd: C, 65.33; H, 3.17; N, 4.01 Found: C, 65.11; H, 3.32; N, 3.94

A solution of the carbonate (2.0 g, 5.73 mmol), produced in the preceding paragraph, in 100 mL of chloroform (ethanol free) was added under nitrogen dropwise over 2 hours to a solution of dodecylamine (1.2 g, 6.47 mmol) and triethylamine (4.0 mL, 28.7 mmol) in 25 mL of chloroform at room temperature. After the addition the reaction was stirred overnight at room temperature. The reaction was extracted with 1N HCl, multiple times with saturated sodium carbonate, dried (MgSO$_4$) and the solvent removed under reduced pressure to give 2.28 g of an off-white solid. Recrystallization of this solid from methylene chloride-diisopropyl ether gave 1.31 g (58%) of the title compound as a white crystalline solid, mp 112°–114° C.

Elemental analysis for $C_{25}H_{33}NO_3$ Cal'd: C, 75.92; H, 8.41; N, 3.54 Found: C, 75.59; H, 8.74; N, 3.80

EXAMPLE 8

Ethylcarbamic acid 2-dibenzofuranyl ester

In the same manner as described in Example 7, and replacing dodecylamine with ethylamine, the title compound was produced as a white crystalline solid (0.63 g, 43%) after recrystallization of the crude reaction mixture from methylene chloride-diisopropyl ether, mp 141°–144° C.

Elemental analysis for $C_{15}H_{13}NO_3$ Cal'd: C, 70.58; H, 5.13; N, 5.49 Found: C, 70.48; H, 5.19; N, 5.43

What is claimed is:

1. A compound of formula A:

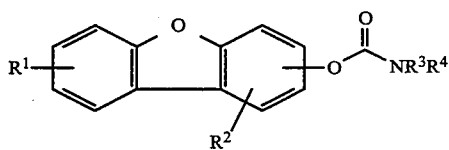

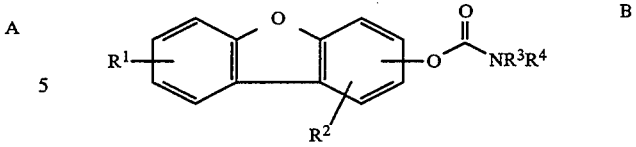

wherein $R^1$ and $R^2$ are, independently, hydrogen, fluorine, chlorine, bromine, iodine, trifluoromethyl, cyano, nitro, $C_1$-$C_6$ alkyl, $C_1$-$C_6$ alkoxy, —$CO_2H$, $C_2$-$C_7$ alkylcarbonyl, $C_2$-$C_7$ alkylcarbonyloxy, $C_2$-$C_7$ alkoxycarbonyl, $C_2$-$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$-$C_6$ alkyl;

$R^4$ is $C_2$-$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl.

2. The compound of claim 1 which is butylcarbamic acid 2-dibenzofuranyl ester.

3. The compound of claim 1 which is (1,5-dimethylhexyl)carbamic acid 2-dibenzofuranyl ester.

4. The compound of claim 1 which is hexylcarbamic acid 2-dibenzofuranyl ester.

5. The compound of claim 1 which is (4-phenylbutyl)carbamic acid 2-dibenzofuranyl ester.

6. The compound of claim 1 which is (cyclohexylmethyl)carbamic acid 2-dibenzofuranyl ester.

7. The compound of claim 1 which is dodecylcarbamic acid 2-dibenzofuranyl ester.

8. The compound of claim 1 which is ethylcarbamic acid 2-dibenzofuranyl ester.

9. A method for reducing cholesterol uptake from the intestinal tract which comprises administering, orally or parenterally, to an animal in need of reduced cholesterol absorption, a compound of formula B:

wherein $R^1$ and $R^2$ are, independently, hydrogen, fluorine, chlorine, bromine, iodine, trifluoromethyl, cyano, nitro, $C_1$-$C_6$ alkyl, $C_1$-$C_6$ alkoxy, —$CO_2H$, $C_2$-$C_7$ alkylcarbonyl, $C_2$-$C_7$ alkylcarbonyloxy, $C_2$-$C_7$ alkoxycarbonyl, $C_2$-$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$-$C_6$ alkyl;

$R^4$ is $C_2$-$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl.

10. A pharmaceutical composition comprising a compound of formula B:

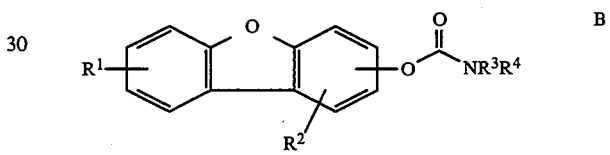

wherein $R^1$ and $R^2$ are, independently, hydrogen, fluorine, chlorine, bromine, iodine, trifluoromethyl, cyano, nitro, $C_1$-$C_6$ alkyl, $C_1$-$C_6$ alkoxy, —$CO_2H$, $C_2$-$C_7$ alkylcarbonyl, $C_2$-$C_7$ alkylcarbonyloxy, $C_2$-$C_7$ alkoxycarbonyl, $C_2$-$C_7$ alkoxycarbonyloxy, mono or di alkylaminocarbonyl in which each alkyl group has 1 to 6 carbon atoms, or mono or di alkylaminocarbonyloxy in which each alkyl group has 1 to 6 carbon atoms;

$R^3$ is hydrogen or $C_1$-$C_6$ alkyl;

$R^4$ is $C_2$-$C_{18}$ alkyl, cycloalkylalkyl where the cycloalkyl moiety has 3 to 8 carbon atoms and the alkyl moiety has 1 to 6 carbon atoms or phenylalkyl of 7 to 18 carbon atoms or substituted phenylalkyl, where the alkyl moiety is 1 to 12 carbon atoms and the substituent on the benzene ring is alkyl of 1 to 6 carbon atoms, alkoxy of 1 to 6 carbon atoms, halo, nitro, cyano, trifluoromethyl or phenyl;

and a pharmaceutically acceptable carrier therefore.

* * * * *